United States Patent
Astier

(10) Patent No.: US 11,939,632 B2
(45) Date of Patent: Mar. 26, 2024

(54) NUCLEIC ACID SEQUENCING USING NANOTRANSISTORS

(71) Applicant: Roche Sequencing Solutions, Inc., Pleasanton, CA (US)

(72) Inventor: Yann Astier, Livermore, CA (US)

(73) Assignee: Roche Sequencing Solutions, Inc., Pleasanton, CA (US)

(*) Notice: Subject to any disclaimer, the term of this patent is extended or adjusted under 35 U.S.C. 154(b) by 0 days.

(21) Appl. No.: 17/731,818

(22) Filed: Apr. 28, 2022

(65) Prior Publication Data

US 2022/0251645 A1 Aug. 11, 2022

Related U.S. Application Data

(62) Division of application No. 16/337,847, filed as application No. PCT/EP2017/074682 on Sep. 28, 2017, now Pat. No. 11,345,961.

(60) Provisional application No. 62/404,732, filed on Oct. 5, 2016.

(51) Int. Cl.
*C12Q 1/68* (2018.01)
*C12Q 1/6823* (2018.01)
*C12Q 1/6869* (2018.01)

(52) U.S. Cl.
CPC ......... *C12Q 1/6869* (2013.01); *C12Q 1/6823* (2013.01)

(58) Field of Classification Search
CPC .... C12Q 1/6869; C12Q 1/6823; G01N 27/42; B01L 2300/0645; B01L 2400/0415; B01L 3/502
See application file for complete search history.

(56) References Cited

U.S. PATENT DOCUMENTS

| 9,708,656 B2 | 7/2017 | Turner et al. |
| 2014/0309144 A1 | 10/2014 | Turner et al. |
| 2015/0111759 A1 | 4/2015 | Ju et al. |
| 2016/0017416 A1 | 1/2016 | Boyanov et al. |

FOREIGN PATENT DOCUMENTS

| JP | 2016-504019 A | 2/2016 |
| WO | 2009/006445 A2 | 1/2009 |
| WO | 2014/074727 A1 | 5/2014 |
| WO | 2014/182630 A1 | 11/2014 |
| WO | 2016/183218 A1 | 11/2016 |
| WO | 2017/024049 A1 | 2/2017 |

OTHER PUBLICATIONS

International Search Report and Written Opinion in PCT/EP2017/074682 dated Nov. 27, 2017; 8 pages.

*Primary Examiner* — Jezia Riley
(74) *Attorney, Agent, or Firm* — Kilpatrick Townsend and Stockton LLP

(57) ABSTRACT

Embodiments may include a nucleic acid molecule system. The system may include a nucleic acid polymerase attached to a tether compound. The polymerase may be configured to elongate a nascent strand. The system may also include a nucleotide attached to a label compound. The label compound may include a moiety. The system may further include a transistor in electrical communication with a power supply. The polymer may be attached to the transistor. In addition, the system may include a meter device configured to measure an electrical characteristic of the transistor from the moiety after the label compound is cleaved from the nucleotide by the nucleic acid polymerase.

17 Claims, 14 Drawing Sheets

NUCLEIC ACID SEQUENCING USING NANOTRANSISTORS

CROSS-REFERENCE TO RELATED APPLICATIONS

This application is a divisional of U.S. patent application Ser. No. 16/337,847 filed Mar. 28, 2019, which is a US National Phase Application under 35 U.S.C. 371 claiming priority to International Patent Application No. PCT/EP2017/074682, filed Sep. 28, 2017, which claims priority to U.S. Provisional Application No. 62/404,732, filed Oct. 5, 2016, the contents of each of which are hereby incorporated by reference in the entirety for any and all purposes.

BACKGROUND

Nanotransistors, transistors with dimensions on the order of nanometers, have been used as chemical or biological sensors (S. Sorgenfrei et al., *Nano Lett.* 11(9):3739-3743 (2011); R. Chen et al., *PNAS* 100(9):4984-4989 (2003); S. Peng et al., Conference Paper for the $3^{rd}$ International Workshop on Structural Health Monitoring available at ionicviper.org/system/files/Carbon%20Nanotube%20Sensor_resource.pdf). Nanotransistors often include solid-state components, and in some cases, solid-state nanotransistors include a semiconductor material between two electrodes. A current is sent through the semiconductor material between the electrodes. An electrical characteristic through the nanotransistor changes based on the presence or proximity of compounds to the nanotransistor. Compounds interacting with the nanometer-scale components on the nanotransistor often change the electrical characteristic and operation of these nanotransistors, allowing the nanotransistors to be used as sensors. Nanotransistors have been considered for nucleic acid sequencing, e.g., in single-molecule sequencing (US Patent Publication No. 2006/0246497 A1). Improvements to the accuracy, precision, operation, efficiency, economics, and/or other aspects of nanotransistor sequencing are addressed by the technology described in this document.

BRIEF SUMMARY

Embodiments of the present technology allows for analyzing nucleic acid molecules using a nanotransistor. A nanotransistor can experience a change in an electrical characteristic, such as a current frequency or a current amplitude, when a molecule is near or contacts the nanotransistor. To analyze a nucleic acid molecule, moieties can be used as labels and attached to nucleotides or other nucleic acid molecule precursors. The nucleotide with the moiety can hybridize to the nucleic acid molecule, and a change in an electrical characteristic can then be measured in the nanotransistor. The moiety may be identified based on the change in electrical characteristic, and then correspondingly the nucleotide associated with the moiety can also be identified. Accordingly, the sequence of the nucleic acid molecule may then be determined.

In some embodiments, to aid in sensing the nucleotide, a polymerase can be tethered to the transistor with a tether compound. The nucleotide is attached to a label compound, which includes the moiety. The polymerase hybridizes the nucleotide with the nucleic acid molecule. The hybridization of the nucleotide may cause the nucleotide to separate from the label compound. After the nucleotide separates from the label compound, a portion of the label compound may bind with a portion of the tether compound. As a result, the moiety may be close enough to the nanotransistor to be detected. The remainder of the label compound may partially or completely separate from the tether compound. The label compound may then bind again to the tether compound and repeat this process. The resulting change in the electrical characteristic in the transistor may help in identifying the moiety. After the label compound completely separates from the tether compound, then another nucleotide with another moiety may be added by the polymerase to the nucleic acid molecule to be sequenced. Embodiments of the present technology may allow for analysis of nucleic acid molecules through electrical characteristics rather than optical characteristics. Additionally, embodiments may also avoid the need for wash cycles in analysis.

Some embodiments may include a method of determining a nucleic acid sequence, e.g., DNA. The method may include elongating a nascent strand by a nucleic acid polymerase attached to a transistor by a tether compound. The nucleic acid polymerase may incorporate a nucleotide attached to a label compound that includes a moiety. The nucleic acid polymerase may also cleave the nucleotide from the nascent strand and the moiety. The method may further include measuring a change in an electrical characteristic of a transistor resulting from the moiety. Additionally, the method may include identifying the nucleotide based on the measured change in the electrical characteristic.

Embodiments may include a nucleic acid molecule system. The system may include a nucleic acid polymerase attached to a tether compound. The polymerase may be configured to elongate a nascent strand. The system may also include a nucleotide attached to a label compound. The label compound may include a moiety. The system may further include a transistor in electrical communication with a power supply. The polymer may be attached to the transistor. In addition, the system may include a meter device configured to measure an electrical characteristic of the transistor from the moiety after the label compound is cleaved from the nucleotide by the nucleic acid polymerase.

Some embodiments may include a method of determining a plurality of nucleic acid sequences. The method may include affixing a template parent strand to a transistor. The method includes elongating a nascent strand by a nucleic acid polymerase. The nucleic acid polymerase may incorporate a nucleotide attached to a label compound that includes a moiety. The polymerase may cleave the nucleotide from the label compound during the elongating of the nascent strand. The nascent strand is hybridized to the template parent strand. The method further includes measuring a change in an electrical characteristic of the transistor resulting from the moiety. In addition, the method includes identifying the nucleotide based on the measured change in the electrical characteristic.

Embodiments may also include a nucleic acid molecule analysis system. The system includes a template parent strand affixed to a transistor. The system also includes a nucleic acid polymerase configured to elongate a nascent strand that is hybridized to the template parent strand. The system further includes a nucleotide attached to a label compound. The label compound may include a moiety. In addition, the system may include a power supply in electrical communication with the transistor. The system may further include a meter device configured to measure an electrical characteristic of the transistor from the moiety after the nucleic acid polymerase cleaves the nucleotide from the label compound.

DEFINITIONS

Figure 1:
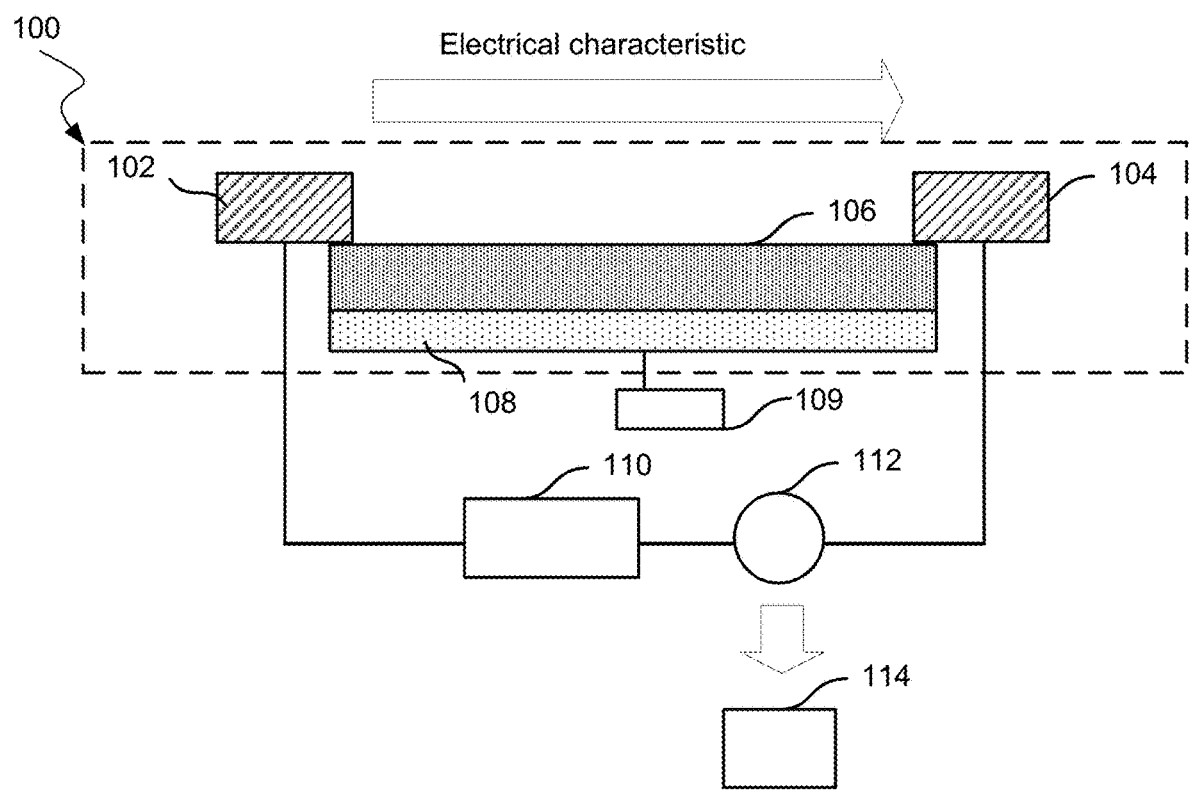
FIG. 1 shows a nanotransistor according to embodiments of the present technology.

"Nucleic acid" may refer to deoxyribonucleotides or ribonucleotides and polymers thereof in either single- or double-stranded form. The term may encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs may include, without limitation, phosphorothioates, phosphoramidites, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, DNA, RNA, oligonucleotide, and polynucleotide.

The term "nucleotide," in addition to referring to the naturally occurring ribonucleotide or deoxyribonucleotide monomers, may be understood to refer to related structural variants thereof, including derivatives and analogs, that are functionally equivalent with respect to the particular context in which the nucleotide is being used (e.g., hybridization to a complementary base), unless the context clearly indicates otherwise.

The term "oscillate" may refer to the motion of an object in a fluid as a result of Brownian motion or other forces. An object may oscillate without active intervention by a person or a machine. In some cases, an object may oscillate as a result of an applied electric field or a pressure-driven flow.

The term "contacting" may refer to bringing one object in proximity to another object such that electrons may tunnel from one object through the other object. At a subatomic level, two objects may never physically touch each other as repulsive forces from electron clouds in the objects may prevent the objects from coming into closer proximity.

The term "moiety" may include a functional group, as the technical term is used in chemistry. In addition, moiety may also refer to an atom or group of atoms bonded together that may form part of a larger compound.

The term "Debye length" may be a measure of the electrical effect of a compound or part of a compound. The Debye length may be the distance over which charges may separate. A longer Debye length may indicate stronger electrical effects.

DETAILED DESCRIPTION

Conventional methods of sequencing include labeling nucleotides with a fluorescent dye. Because of the limits of dyes available and the optical limits of distinguishing between different dyes, dyes need to be washed away periodically, including after each use of a labeled nucleotide. A different dye for a different nucleotide may then be introduced. Washing the dyes away may reduce efficiency of sequencing.

Solid-state transistors provide a promising system for analyzing molecules, including the sequencing of nucleic acid molecules. These solid-state transistor may be on the scale of nanometers or under 0.1 micron, which are referred to as nanotransistors. As examples, nanotransistors may include carbon nanotube transistors, graphene transistors, semiconducting transition metal dichalcogenide 2D crystal transistors (e.g., $MoS_2$, $MoSe_2$, $WS_2$, $WSe_2$, $MoTe_2$, $WTe_2$, $TeS_2$, $SnSe_2$, $TeSe_2$), or silicon nanowire transistors. One or more nanotransistors can be positioned on a substrate, with each nanotransistor being used to sequence a nucleic acid molecule.

Molecules close to or in contact with a nanotransistor may affect the drain current or other electrical characteristics of the nanotransistor. When analyzing nucleic acid molecules and other molecules, water is typically used as the medium. Water is a polar solvent and has a Debye length of under 1 nm. Water may therefore reduce the influence of a molecule on a nanotransistor at a given distance compared to other media. As a result, any molecule to be analyzed may have to be within very close proximity of the nanotransistor. The molecule may be in direct contact with the nanotransistor. In a liquid medium, the probability of a free molecule being in close proximity or contact with a stationary nanotransistor for a sufficient duration to measure an appreciable signal is low, making identifying even a single small molecule challenging.

Larger molecules may have different effects on a nanotransistor, depending on what portion of the molecule is closest to the nanotransistor. Nanotransistors could be used to identify specific portions of a molecule. To sequence a nucleic acid molecule, several nucleotides in the nucleic acid molecule, not just one nucleotide, need to be identified. As a result, several nucleotides in the same nucleic acid molecule, not just one nucleotide, have to be within the close proximity of the nanotransistor in order to be identified by the nanotransistor. Identifying several nucleotides in the same nucleic acid molecule by the nanotransistor would therefore have an even lower probability than identifying a single nucleotide or small molecule. Furthermore, when a nucleotide hybridizes to the nucleic acid molecule, the label may be separated from the nucleotide, reducing the likelihood that the label may be sensed by the nanotransistor. The technology described in this document increases the duration and probability of a molecule being in proximity with the nanotransistor by attaching the nucleic acid molecule to a tether compound affixed to the transistor.

I. Sequencing with Nanotransistors

FIG. 1 shows a nanotransistor 100. Nanotransistor 100 includes a source electrode 102 and a drain electrode 104. Source electrode 102 and drain electrode 104 are connected by a semiconducting material 106. Semiconducting material 106 does not allow current to flow between source electrode 102 and drain electrode 104 unless a voltage is applied to gate electrode 108. The voltage may be supplied by a voltage supply 109. Semiconducting material may include a carbon nanotube, graphene, a semiconducting transition metal dichalcogenide 2D crystal (e.g., $MoS_2$, $MoSe_2$, $WS_2$, $WSe_2$, $MoTe_2$, $WTe_2$, $TeS_2$, $SnSe_2$, $TeSe_2$), or a silicon nanowire. A current, provided by power supply 110, may then flow between source electrode 102 and drain electrode 104. An electrical characteristic, such as current or voltage, through the semiconducting material may be measured by meter 112. The electrical characteristic may change based on the presence of compounds near semiconducting material 106. Electrical characteristic data are analyzed by a computer system 114.

Figure 2:
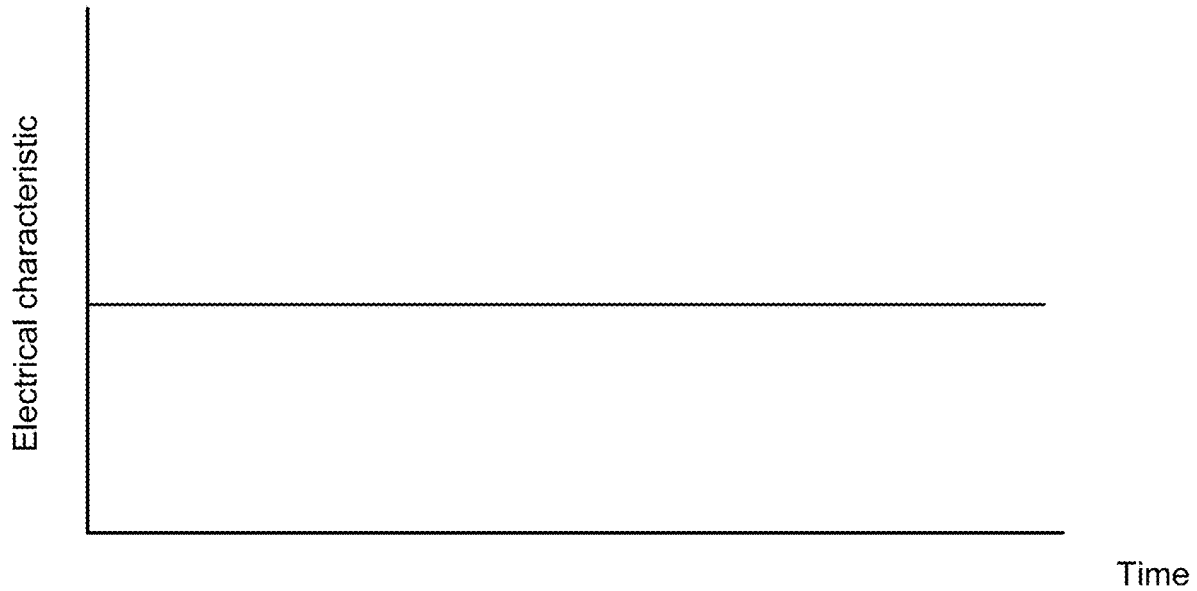
FIG. 2 shows a graph of an electrical characteristic from a nanotransistor according to embodiments of the present technology.

FIG. 2 shows a simplified illustration of the current through nanotransistor 100. An electrical characteristic is shown on the y-axis and time on the x-axis. The electrical characteristic remains constant over time as no compounds are near semiconducting material 106.

Figure 3:
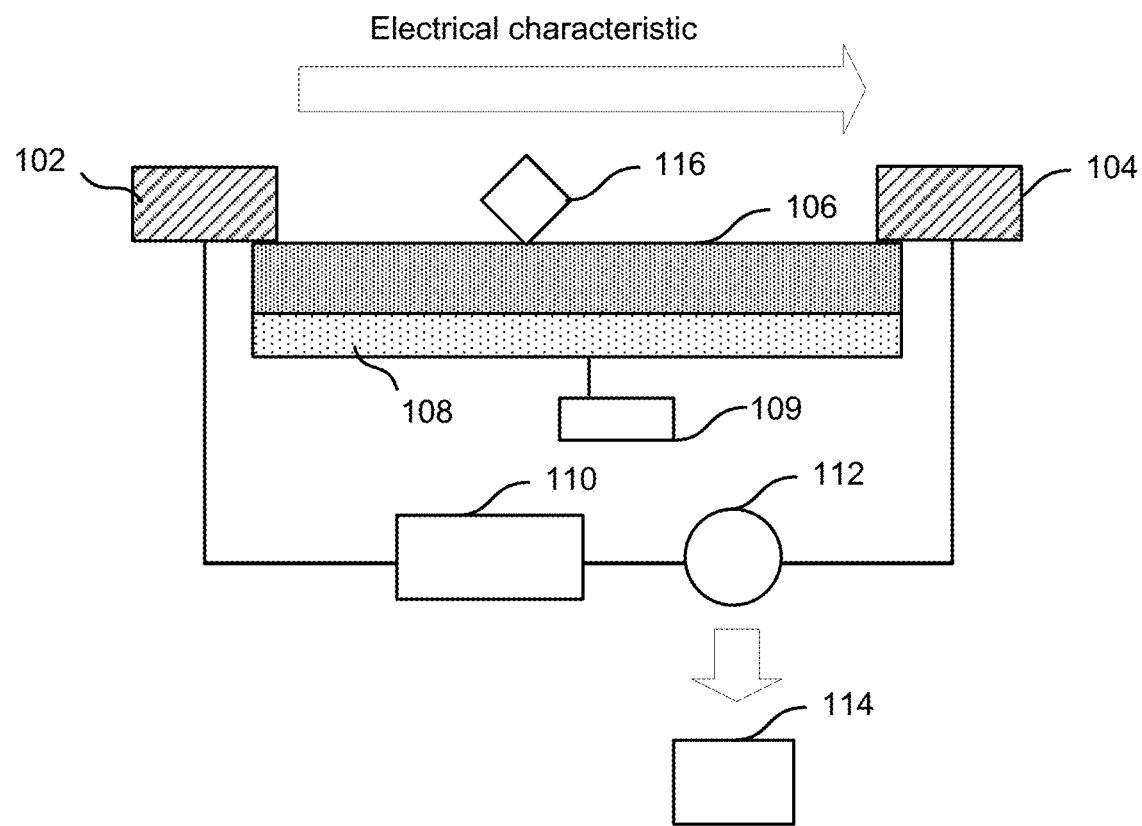
FIG. 3 shows a nanotransistor with a compound on the semiconducting material of the nanotransistor according to embodiments of the present technology.

FIG. 3 shows nanotransistor 100, with a compound 116 on semiconducting material 106. Compound 116 may have dimensions on the same order as the dimensions of semiconducting material 106. Compound 116 may have a characteristic size on the order of 1 nm, 10 nm, 100 nm, or 1 µm. Compound 116 may be a compound with strong electrostatic field effects. For these or other reasons, compound 116 may affect the electrical characteristic between source electrode 102 and drain electrode 104.

Figure 4:
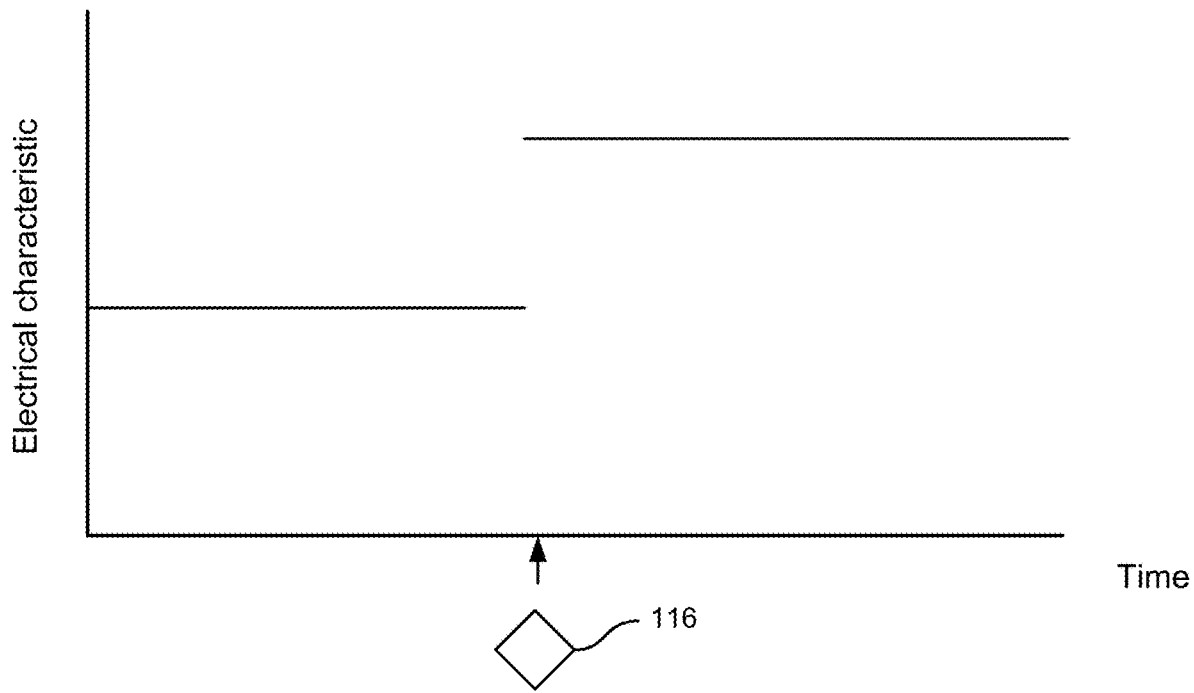
FIG. 4 shows a graph of an electrical characteristic from a nanotransistor before and after a compound is in contact with the semiconducting material of the nanotransistor according to embodiments of the present technology.

FIG. 4 shows a simplified illustration of the current through nanotransistor 100, with the instantaneous addition of compound 116 on semiconducting material 106. In this illustration, compound 116 has the effect of instantaneously increasing the electrical characteristic through nanotransistor 100. In some embodiments, a compound may decrease the electrical characteristic through nanotransistor 100.

The current through nanotransistor 100 or other electrical characteristics of nanotransistor 100 may depend on the identity of compound 116. Different compounds may have different effects on the current or other electrical characteristics through nanotransistor 100. Moreover, different compounds may move at different speeds toward or away from nanotransistor 100, which may be the result of electrostatic or fluidic or other forces acting on the compound. In practice, compound 116 would not instantaneously appear on semiconducting material 106, and as a result, the electrical characteristic would not immediately change as a step function as shown in FIG. 4.

Because different compounds may result in different electrical characteristics measured through nanotransistor 100, nanotransistor 100 may be used to identify different compounds. In particular, a nanotransistor could be used to sequence a nucleic acid molecule. A nucleic acid molecule includes a combination of nucleotides. Each nucleotide of the nucleic acid molecule could be identified using a nanotransistor if each nucleotide was close enough to the nanotransistor for a sufficient duration and the effect of the nucleotide on the nanotransistor can be distinguished from effects of neighboring nucleotides. The sequence could then be determined based on the identity of nucleotides. As described below, the sequence can also be determined from a label compound that is attached to a nucleotide, where different types of nucleotides (e.g., C, T, A, and G) have different label compounds, thereby allowing the sequence to be determined.

II. Nucleic Acid Sequencing with a Tethered Polymerase

To increase the probability and the duration of a nucleotide to remain in the proximity of a nanotransistor, a nucleic acid polymerase may be tethered to the nanotransistor. The tethering allows for nucleotides to be incorporated into a nascent strand while being near enough to the nanotransistor to affect the electrical characteristic through the nanotransistor (as in FIGS. 3 and 4). A compound may tether the polymerase to the nanotransistor.

Tethering a polymerase alone may not allow the nucleotide to be close enough to the nanotransistor in order to affect the electrical characteristic of the nanotransistor. Instead of moving the nucleotide close to the nanotransistor, the nucleotide can be labeled with a polymer, with the polymer attached to a moiety. The moiety induces a strong field disruption in the nanotransistor at a close enough proximity. The polymer may include a single-stranded nucleic acid that at least partially hybridizes with the compound that tethers the polymerase to the nanotransistor. In this manner, after a triphosphate of the nucleotide hydrolyzes, the polymer and the moiety are separated from the nucleotide. The polymer can bind with the compound tethering the polymerase to the nanotransistor, The binding of the polymer to the compound (i.e., the tether compound) brings the moiety closer to the nanotransistor, affecting the conductance of the nanotransistor. A change in an electrical characteristic can then be measured. The moiety may not only affect the amplitude of current through the nanotransistor, but because of the particular binding involved, may also oscillate at a certain frequency. The amplitude and frequency of the current through the nanotransistor may help identify the nucleotide.

A. System with Tethered Polymerase

Figure 5:
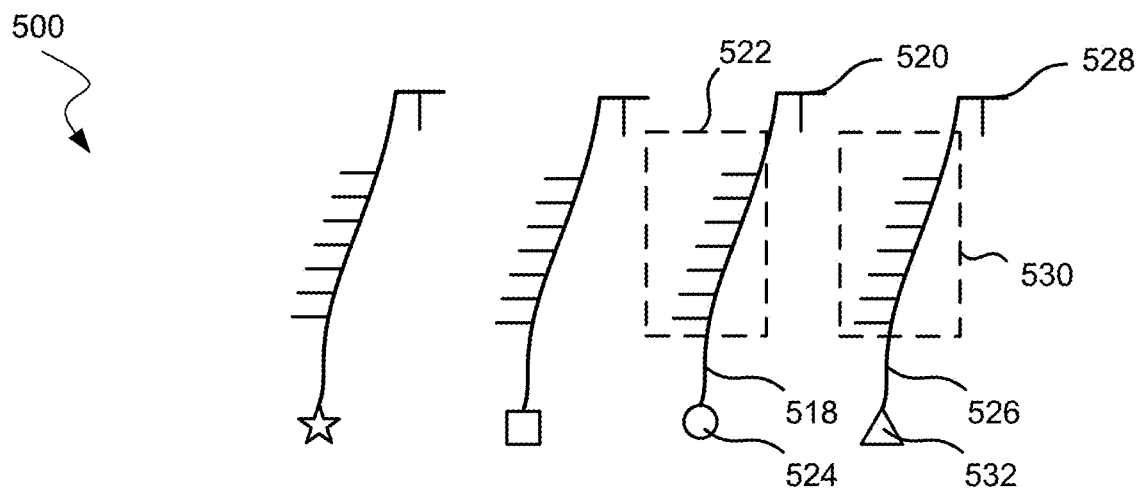
FIG. 5 shows a nucleic acid analysis system according to embodiments of the present technology.
Figure 5:
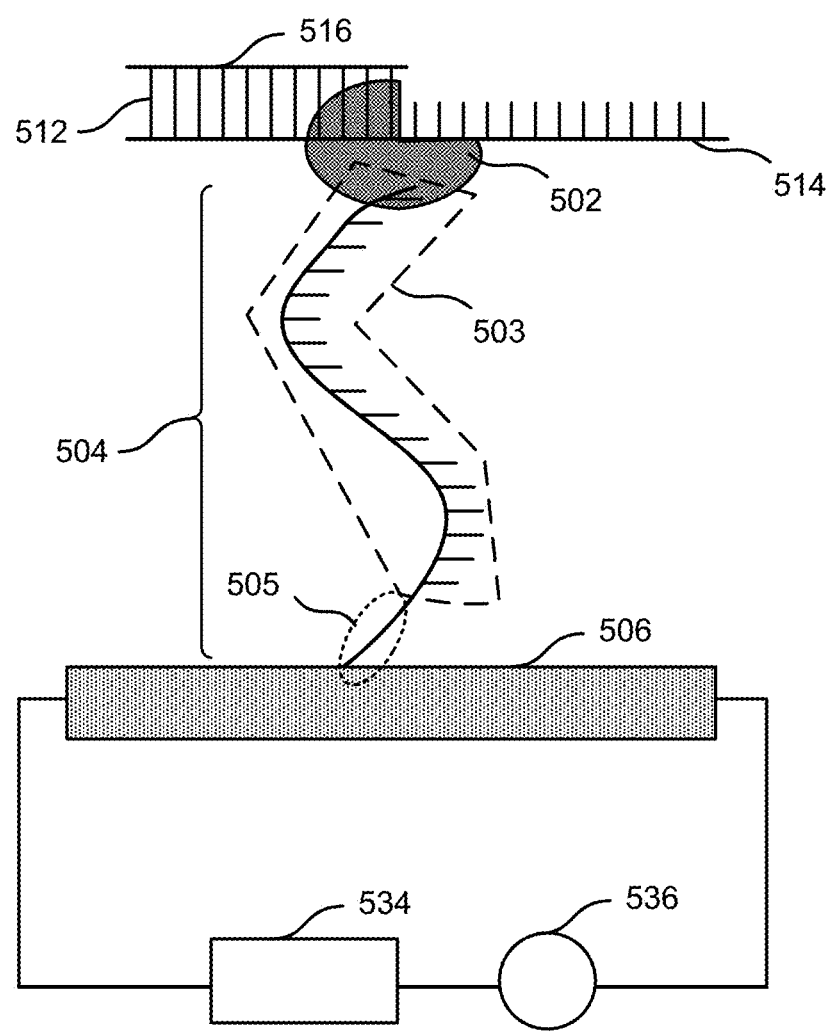
Figure 6:
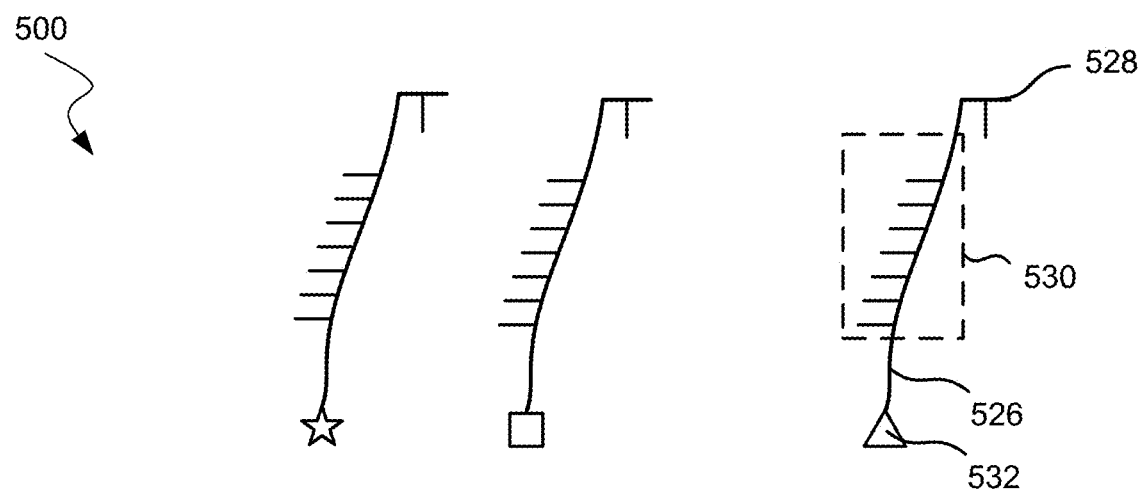
FIG. 6 shows a nucleic acid analysis system with a moiety in contact with a nanotransistor according to embodiments of the present technology.
Figure 6:
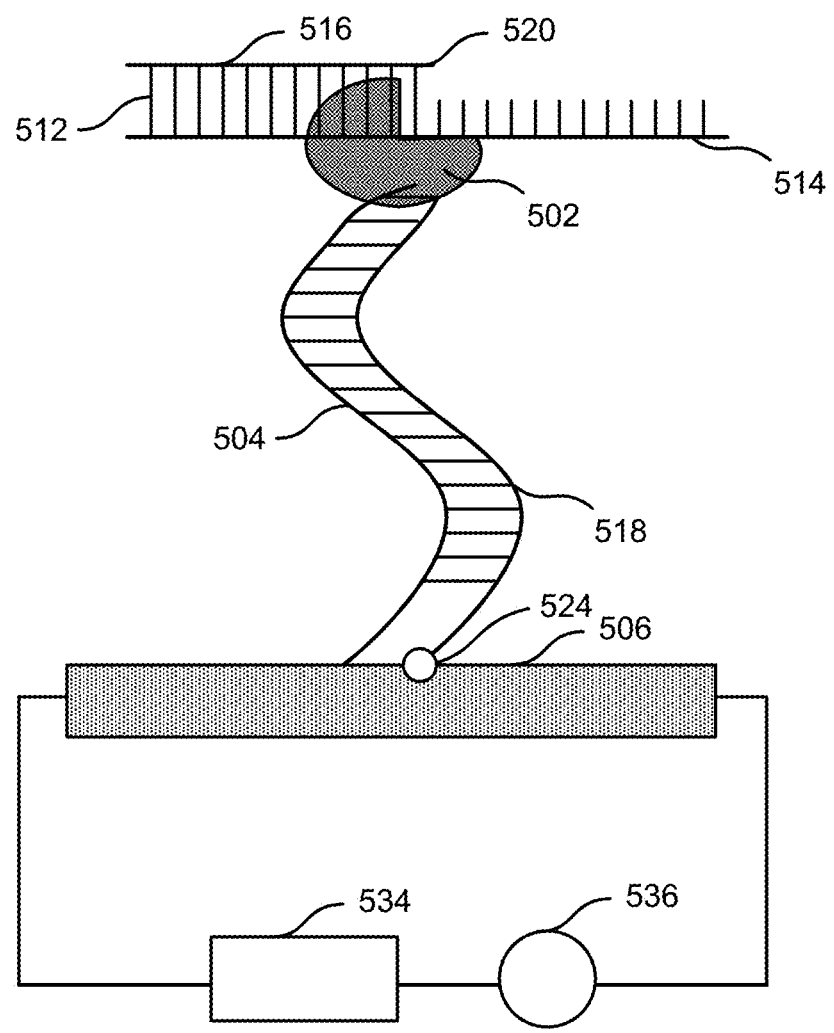

FIGS. 5 and 6 show a nucleic acid analysis system 500 according to embodiments of the present technology. As shown, system 500 includes a nucleic acid polymerase 502 affixed to a tether compound 504 that attaches nucleic acid polymerase 502 to a transistor 506. Nucleic acid polymerase 502 may be bound covalently to tether compound 504. Transistor 506 may be a nanotransistor 100 or any transistor described herein. Nucleic acid polymerase 502 is configured to elongate a nascent strand 516. Nascent strand 516 is hybridized to a template parent strand 514. Nascent strand 516 and template parent strand 514 form intermediate nucleic acid molecule 512. Tether compound 504 includes a nucleic acid strand 503 (i.e., a first nucleic acid strand) and a polymer 505.

In FIG. 5, the polymer 505 is depicted as the portion of tether compound 504 in contact with transistor 506, and the nucleic acid strand 503 is depicted as the portion of tether compound 504 with horizontal lines off the main line of tether compound 504. Polymer 505 may include polyethylene glycol, a peptide, or a biological polymer. Polymer 505 may have a specific affinity for another polymer of a similar nature. For example, polymer 505 may be a short peptide that has a known affinity for another peptide. The peptide may have a certain sequence and may be used to interact with an oligonucleotide of a specific sequence. Nucleic acid strand 503 may be an oligonucleotide.

System 500 may include nucleotides, such as nucleotide 520, that may hybridize with template parent strand 514 and may be incorporated into nascent strand 516. Nucleotide 520 is attached to first label compound 518, which includes a nucleic acid strand 522 (i.e., a second nucleic acid strand) and a moiety 524. Moiety 524 may have a strong electric field or otherwise a strong field effect on transistor 506 when within the Debye length of transistor 506. For example, moiety 524 may be a metal cluster, a halogen, or a redox agent. A metal cluster may include a multi-metal organometallic compound or a metal nanoparticle. Moiety 524 may be limited to one of these categories, may exclude any of these categories, or may be a combination of these categories. At least one of moiety 524 or nucleic acid strand 522 may serve to label the particular type of nucleotide. For example, the system may also include a nucleotide 528 attached to a second label compound 526, which includes a nucleic acid strand 530, and a moiety 532, but with nucleotide 528 and moiety 532 different from nucleotide 520 and moiety 524, respectively, in first label compound 518. Different moieties may be used in order to help identify different nucleotides. In some embodiments, different nucleotides may be labeled with identical moieties but different nucleic acid strands. In these embodiments, the different nucleic acid strands may affect the oscillation or movement of the moiety, and as a result, affect the change in electrical characteristic in transistor 506.

Nucleic acid strand 522 in first label compound 518 and nucleic acid strand 530 in second label compound 526 may be the same for different nucleotides 520 and 528, or in some cases, may be different for different nucleotides 520 and 528. Different nucleic acid strands may include sequences with a different number of mismatches, which may then affect the binding of the label compound with the tether compound. A greater number of mismatches may increase the oscillations of the moiety. If nucleic acid strands are different for different nucleotides, the moieties may be the same or different for different nucleotides. With four different nucleotides for DNA (A, T, C, G), the system may include four different compounds with four different moieties—one for each type of nucleotide. The system may include a plurality of these compounds, and each type of compound may be one of a plurality of these compounds. In some cases, either or both of the tether compound and the label compound may not include nucleic acid strands, particularly if a portion of the tether compound has an affinity for a portion of the label compound. For example, both the tether compound may have a peptide that has an affinity for a peptide on the label compound.

Transistor 506 may be in electrical communication with a power supply 534. Tether compound 504 may be affixed to transistor 506, and tether compound 504 may contact transistor 506 with the polymer portion of tether compound 504. Power supply 534 may be a direct current power supply or an alternating current power supply.

In addition, system 500 may include a meter device 536 configured to measure an electrical characteristic of 506 transistor from moiety 524 after nucleotide 520 hybridizes with nascent strand 514. First label compound 518 detaches from nucleotide 520, and nucleic acid strand 522 hybridizes with nucleic acid strand 503.

FIG. 6 shows system 500 after tether compound 504 has hybridized with a portion of first label compound 518. Nucleotide 520 has been incorporated into nascent strand 516, and nucleotide 520 has hybridized with template parent strand 514. Hydrolysis of a triphosphate in nucleotide 520 results in the separation of nucleotide 520 from first label compound 518. After separation of nucleotide 520, nucleic acid strand 522 hybridizes with tether compound 504 because nucleic acid strand 503, and nucleic acid strand 522 may have complementary or substantially complementary sequences. Hybridizing tether compound 504 to the remainder of first label compound 518 may bring moiety 524 closer to transistor 506. In some cases, moiety 524 may contact transistor 506. Moiety 524 may not be fixed in one location. Moiety 524 may move toward and away from transistor 506. In other words, moiety 524 may oscillate. Tether compound 504 may partially or fully de-hybridize, and in some cases re-hybridize, with the remainder of first label compound 518. This process of hybridizing and de-hybridizing may also result in moiety 524 oscillating to and from transistor 506. Eventually, the remainder of first label compound 518 may fully de-hybridize, forming a system similar to FIG. 5. Nascent strand 516 may accept another nucleotide for further elongation. For example, nucleotide 528 may be incorporated into nascent strand 516.

The nucleic acid molecule analysis system may include a plurality of transistors. The power supply may be in electrical communication with the plurality of transistors, which may include sending current to each transistor. An electrical characteristic, such as current or voltage, through the transistors may be measured by a single meter device equipped to measure the electrical characteristic of many transistors in parallel, or the electrical characteristic through the transistors may be measured by a plurality of meter devices, with a respective meter device for each transistor. Millions or hundreds of millions of transistors may make up the plurality of transistors. The plurality of transistors may allow for multiplexing, which may be more efficient and more accurate than conventional systems and methods. Semiconductor fabrication methods may make nanotransistors low cost, even if hundreds of millions of nanotransistors are included in a system.

B. Method with Tethered Polymerase

Figure 7:
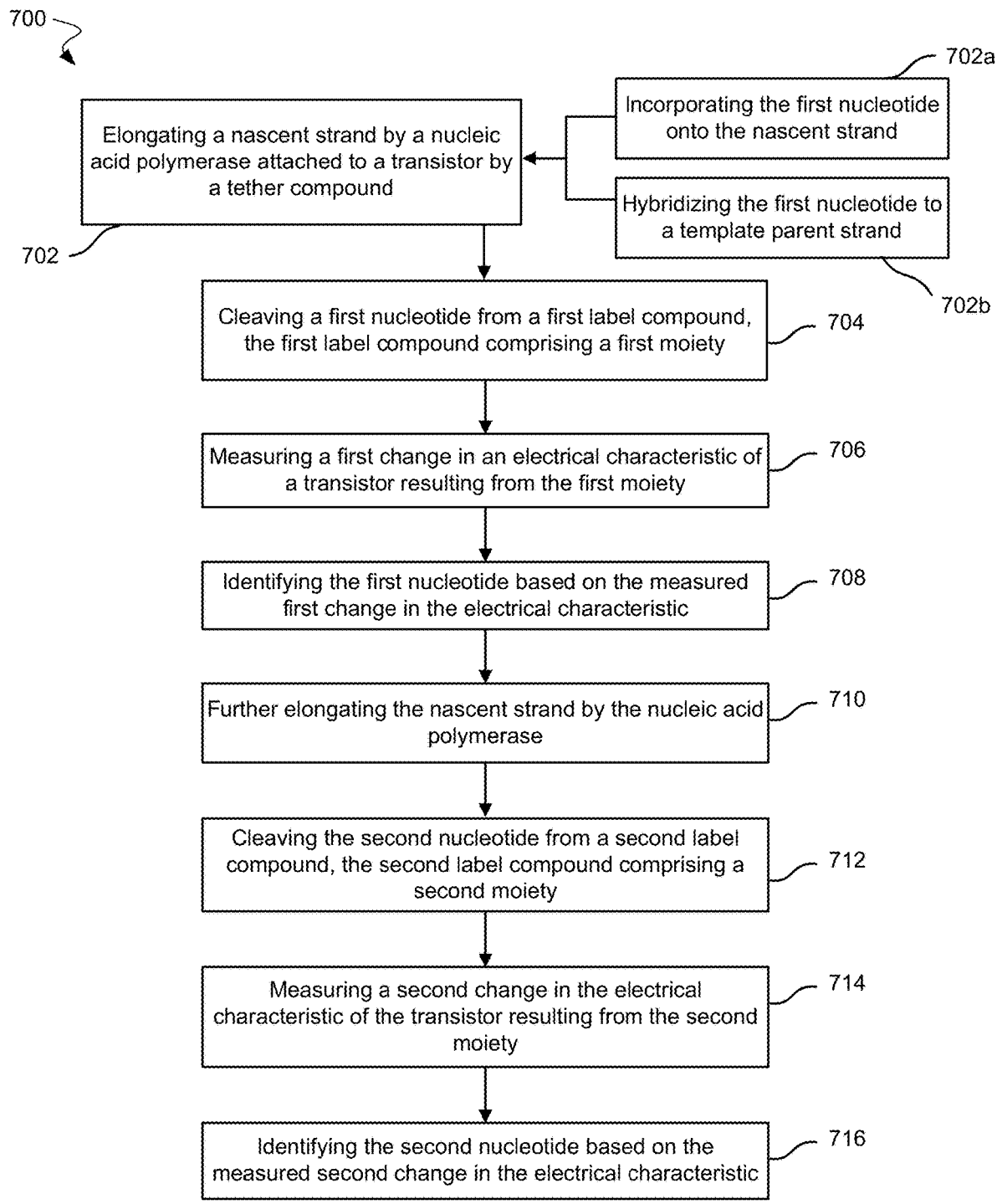
FIG. 7 show a method of determining a nucleic acid sequence according to embodiments of the present technology.

FIG. 7 show a method of analyzing a nucleic acid strand according to embodiments of the present technology. The nucleic acid sequence may be a partial or full sequence of DNA. System 500 may be used with method 700.

In block 702, method 700 includes elongating a nascent strand by a nucleic acid polymerase attached to a transistor by a tether compound. The nascent strand may be hybridized to a template parent strand.

Block 702a includes incorporating a first nucleotide into the nascent strand and may be one part of elongating the nascent strand. The nucleotide may be nucleotide 520 in FIG. 5.

Block 702b includes hybridizing the first nucleotide to the template parent strand. Block 702b may be an operation in elongating the nascent strand. The first nucleotide may be attached to a first label compound comprising a moiety. The label compound may also include a first nucleic acid strand that is attached to a moiety. The moiety may be any moiety described herein, including moiety 524. The first label compound may include first label compound 518 in FIG. 5.

The nucleic acid polymerase may be attached to the transistor by a compound, such as tether compound 504. The tether compound may include a second nucleic acid strand. The tether compound may include a polymer. The polymer may contact and be affixed to the transistor. The polymer may be any polymer described herein.

In block 704, the first nucleotide may be cleaved from the first label compound, which includes the first moiety. The nucleic acid polymerase may cleave the nucleotide from the first label compound because the first label compound may be attached to a triphosphate group of the nucleotide. When the triphosphate is hydrolyzed as the nucleotide is added to the nascent strand, the first label compound may separate from the nucleotide. A portion or all of the second nucleic acid strand of the tether compound may bind or hybridize with the first nucleic acid strand of the first label compound. For example, as shown in FIG. 6, nucleotide 520 may be added to nascent strand 516. Tether compound 504 and a portion of first label compound 518 may bind together. This binding may allow for moiety 524 to stay in contact with or within the Debye length of transistor 506 for a longer period of time than without such binding. Moiety 524 may move closer to or away from the nanotransistor, which may affect the electrical characteristic. Moiety 524 may move in contact or out of contact with the nanotransistor. In some cases, the moiety may oscillate near the nanotransistor.

In block 706, method 700 further includes measuring a first change in an electrical characteristic of a transistor resulting from the moiety. The electrical characteristic may be current or voltage. The electrical characteristic may include at least one of an amplitude or frequency of the current or voltage. The frequency may be measured while the moiety oscillates near the nanotransistor. In some cases, the oscillation may be a result of at least one of electrical fields or Brownian motion. The oscillation may also be a result of the temporary hybridizing of the nucleic acid sequence in the first label compound to the nucleic acid sequence of the tether compound, as shown in FIG. 6. The hybridizing and de-hybridizing may be a result of the electrical characteristics of the transistor, including the transistor potential, and/or the characteristics of the fluid. The measured change in the electrical characteristic may result from the moiety starting contact with the transistor, contacting the transistor, ending contact with the transistor, or any combination thereof. The measured change in the electrical characteristic may be related to the amount (e.g., surface area) or strength of contact between the moiety and the transistor.

In block 708, method 700 includes identifying the nucleotide based on the measured first change in the electrical characteristic. A computer system may be used in analyzing the electrical characteristic pattern and identify the nucleotide.

Because the nucleotide incorporated by the polymerase into the nascent strand is complementary to the nucleotide on the template parent strand, the complementary nucleotide on the template parent strand may also be identified. For example, in FIG. 6, nucleotide 520 may be identified, which would also lead to the identification of the complementary nucleotide on template parent strand 514. Either nucleotide may be part of the nucleic acid sequence that is determined by methods described herein.

First nucleic acid strand of the first label compound may be separated from the second nucleic acid strand of the tether compound. The transistor potential may have the effect of melting the two hybridized strands, which results in separation. The first label compound may then move or diffuse away from the nanotransistor into the background, such that the effect of the moiety on the nanotransistor can no longer be measured. In other words, the moiety may move farther than the Debye length away from the nanotransistor. After the first label compound separates and moves away, the second nucleic acid strand of the tether compound may be free to hybridize with another nucleic acid strand.

In block 710, the nascent strand is further elongated by the nucleic acid polymerase. The nucleic acid polymerase incorporates a second nucleotide into the nascent strand. The second nucleotide may be attached to a second label compound, which may include a third nucleic acid strand that is attached to a second moiety. The second nucleotide may be different from the first nucleotide. As discussed above, a different label compound, including a different moiety and/or a different nucleic acid strand, may be used in methods to help identify different nucleotides. The third nucleic acid strand of the second label compound may include the same sequence as the first nucleic acid strand of the first label compound. The same sequence may allow for hybridizing to the tether compound.

In block 712, a second nucleotide may be cleaved from the second label compound. The nucleic acid polymerase may cleave the second nucleotide after a triphosphate is hydrolyzed. As with the first label compound before, the second label compound may then be free to move to hybridize with the tether compound. Hybridizing with the tether compound may then allow the second moiety to affect the electrical characteristic of the transistor.

In block 714, a second change in the electrical characteristic of the transistor resulting from the second moiety may be measured. The change in electrical characteristic may be any change described herein.

In block 716, method 700 may include identifying the second nucleotide based on the measured second change in the electrical characteristic. The second change in the electrical characteristic resulting from the second moiety may be different from the first change in the electrical characteristic resulting from the first moiety. A computer system may be used in identifying the nucleotides in the nucleic acid sequence.

A second nucleic acid polymerase may be attached to the transistor by a second compound (e.g., a second tether compound) affixed to the transistor. The second tether compound may include another nucleic acid strand and a second polymer. The second polymer may be affixed to the transistor. The second nucleic acid polymerase may allow for an additional nucleotide of label compounds to hybridize, which may increase the effect on the electrical characteristic. In addition, a plurality of nucleic acid polymerases, including more than two nucleic acid polymerases, may be attached to the transistor by a plurality of tether compounds.

Figure 8:
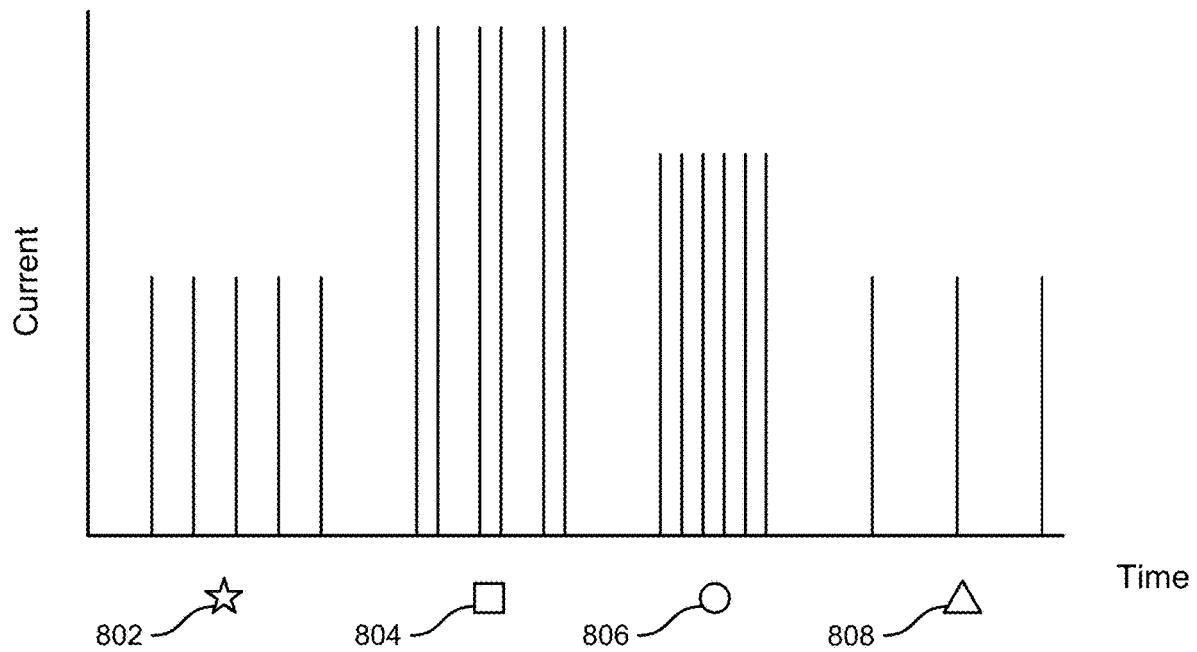
FIG. 8 shows changes in current resulting from different moieties according to embodiments of the present technology.

FIG. 8 shows an illustration of how different moieties may result in different changes in electrical characteristics. A different nucleotide may be labeled with a different moiety. For example, an A nucleotide may always be associated with moiety 802, a C nucleotide may always be associated with moiety 804, a G nucleotide may always be associated with moiety 806, and a T nucleotide may always be associated with moiety 808. Each moiety may have a different effect on the current or voltage through the transistor. As shown in FIG. 8, the differences in electrical characteristic can manifest as differences in amplitude, frequency, and or duration. The electrical characteristic may be current or voltage. The differences in amplitude, frequency, or duration of the electrical characteristic may be a result of the nucleic acid strand of the label compound, with changes in the sequence for different nucleotides affecting the strength of binding between the tether compound and the label compound. The electrical characteristics of the different label compounds and/or moieties may form an electrical fingerprint for the nucleotides. A computer system may analyze the change in electrical characteristics against a reference change in electrical characteristic in order to identify the moiety and therefore the nucleotide. The reference change in electrical characteristic may be determined empirically or may be calculated based on atomic and molecular properties.

C. Example

A nucleic acid analysis system, similar to system 500, is used to sequence nucleic acid molecules. The different types of nucleotides are labeled with different moieties. The different moieties, when in proximity of the nanotransistor, show different current signatures. As a result, the nucleotides are identified by the current patterns in the nanotransistor.

III. Multiple Nucleic Acids on Nanotransistor

In some embodiments, multiple copies of a nucleic acid strand or single-stranded oligonucleotide may be attached (tethered) to a nanotransistor. The multiple copies of the nucleic acid strand allow for simultaneous or nearly simultaneous addition of multiple nucleotides, where each may be labeled with the same moieties. The effect of the moiety on the nanotransistor may therefore be multiplied and concentrated, allowing for a stronger signal in the electrical characteristic of the nanotransistor than if only a single moiety was used.

Multiple polymerases may be used for each of the multiple copies of the nucleic acid strand. With the multiple copies of the nucleic acid strand attached to the nanotransistor, the polymerases may not need to be tethered to the nanotransistor. Without a tether compound to tether the polymerase to the nanotransistor, the label compounds with the moieties do not need to be configured to hybridize with a tether compound. As a result, the nucleotides and moieties may not be attached to a nucleic acid strand.

A. Systems with Tethered Nucleic Acids

Figure 9:
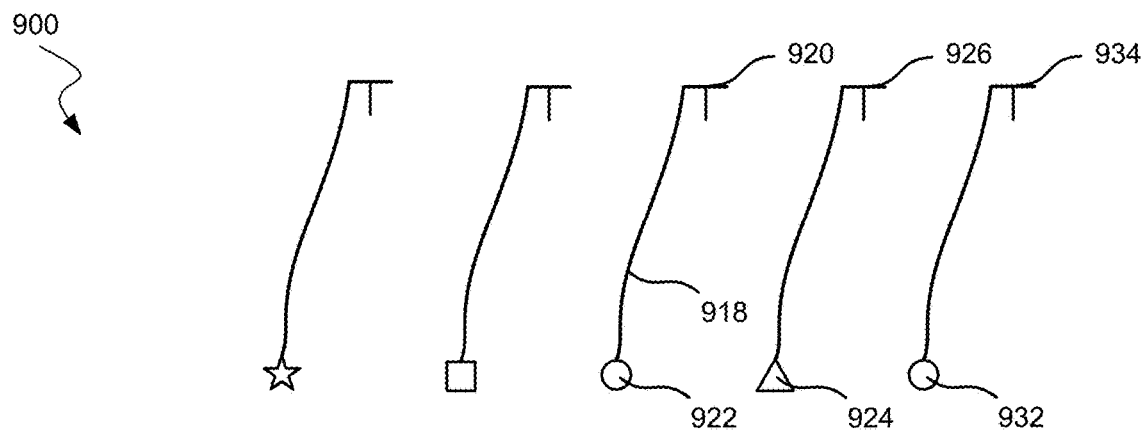
FIG. 9 shows a nucleic acid analysis system according to embodiments of the present technology.
Figure 9:
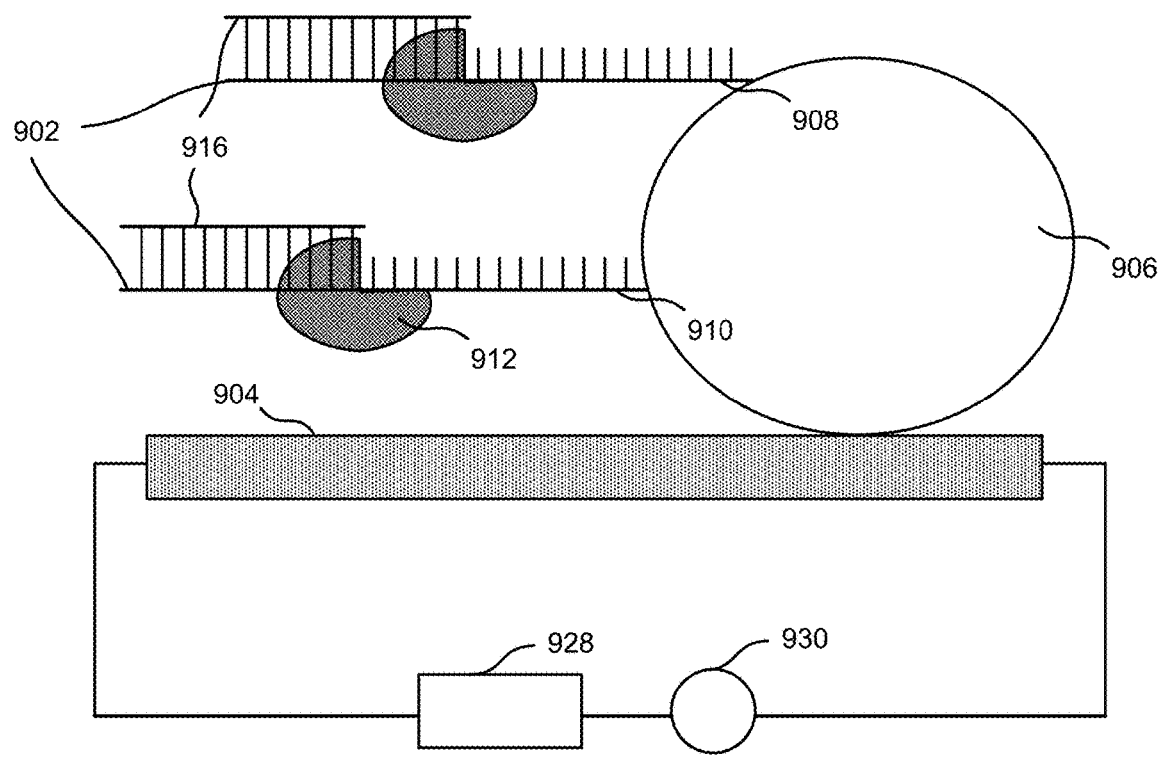

FIG. 9 shows an embodiment of a nucleic acid molecule analysis system 900. System 900, as one of skill may note, may be similar to system 500, described previously. System 900 may include a template parent strands 902 affixed to a nanotransistor 904. Nanotransistor 904 may be nanotransistor 100 or any transistor described herein. Template parent strands 902 may directly contact nanotransistor 904, or, as shown in FIG. 9, template parent strands 902 may be affixed to a particle 906. Particle 906 may be affixed to nanotransistor 904. In some embodiments, particle 906 may be affixed to a polymer, which may be affixed to nanotransistor 904. Although FIG. 9 shows multiple template parent strands 902, system 900 may include only a single template parent strand affixed to nanotransistor 904.

Particle 906 may be a bead or may be spherical. Particle 906 may also be considered a tether compound. If particle 906 is not spherical, particle 906 may have a characteristic dimension. Particle 906 may have a diameter or characteristic dimension in a range from 10 nm to 15 nm, 15 nm to 20 nm, 20 nm to 30 nm, 30 nm to 40 nm, 40 nm to 50 nm, or 50 nm or more in embodiments.

Template parent strands 902 may include first template parent strand 908 and second template parent strand 910. The template parent strands may include 3, 4, 5, or more template parent strands. Each template parent strand may include an identical nucleotide sequence. The identical nucleotide sequence may include all the nucleotides in each template parent strand or may include a subset of the nucleotides in each template parent strand.

System 900 may also include a polymerase 912 configured to promote elongating nascent strands 916 using template parent strands 902. In some cases, nucleic acid polymerase 912 may be tethered to nanotransistor 904 or particle 906 with a compound similar to any tether compound described herein. In some cases, nucleic acid polymerase 912 may not be tethered to nanotransistor 904 and may instead freely move within the aqueous medium. In cases where nucleic acid polymerase 912 is tethered to nanotransistor 904 or particle 906, the tether compound may comprise a nucleic acid strand that binds or hybridizes with at least a portion of the label compound, similar to embodiments described above and in FIGS. 5 and 6. However, not tethering the nucleic acid polymerase to the nanotransistor may simplify the system by not requiring a tether compound for the nucleic acid polymerase and not configuring a label compound to bind with the tether compound.

System 900 may further include a plurality of label compounds. Nucleotide 920 may be attached to a label compound 918, which includes a moiety 922. As with FIGS. 5 and 6, a different moiety may be associated with a different nucleotide, and each type of nucleotide may have the same moiety attached. For example, nucleotide 926, which is different from nucleotide 920, is labeled with a compound that includes moiety 924, which is different from moiety 922. Label compound 918 may be any label compound described herein, and nucleotide 920 may be any nucleotide described herein. Moiety 932, which is the same as moiety 922, is shown as labeling nucleotide 934, which is the same nucleotide as nucleotide 920.

In addition, system 900 may include a power supply 928 in electrical communication with nanotransistor 904. Power supply 928 may be any power supply described herein.

System 900 may further include a meter device 930 configured to measure an electrical characteristic of nanotransistor 904 from a plurality of moieties after the plurality of moieties attaches to and then separates from the nascent strands. Meter device 930 may be any meter device described herein.

Figure 10:
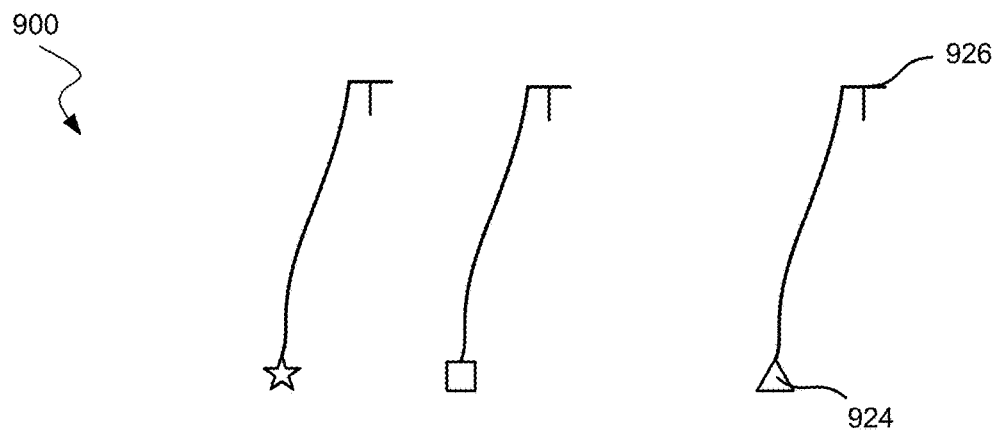
FIG. 10 shows a nucleic acid analysis system with moieties in contact with a nanotransistor according to embodiments of the present technology.
Figure 10:
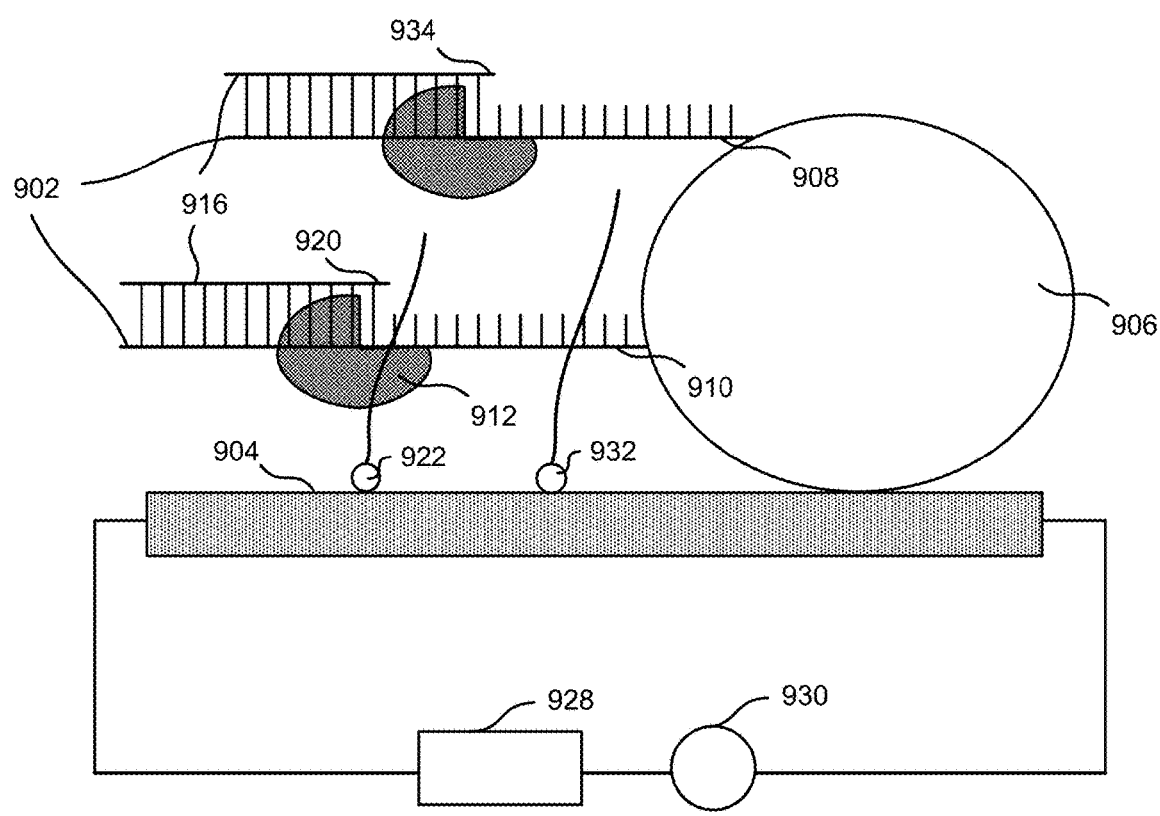

FIG. 10 shows system 900 after nucleotide 920 and nucleotide 934 hybridize with template parent strands 902. Moiety 922 and moiety 932 separate from the nucleotides and move into close proximity or in contact with nanotransistor 904. Meter device 930 can then measure the change in electrical characteristic resulting from the moieties. The nucleotides that hybridized with the plurality of nucleic acid strands may then be identified.

The nucleic acid molecule analysis system may include a plurality of nanotransistors. As with system 500, system 900 may include a plurality of nanotransistors in electrical communication with a single power supply. The plurality of nanotransistors may allow for multiplexing.

B. Methods with Tethered Nucleic Acids

Figure 11:
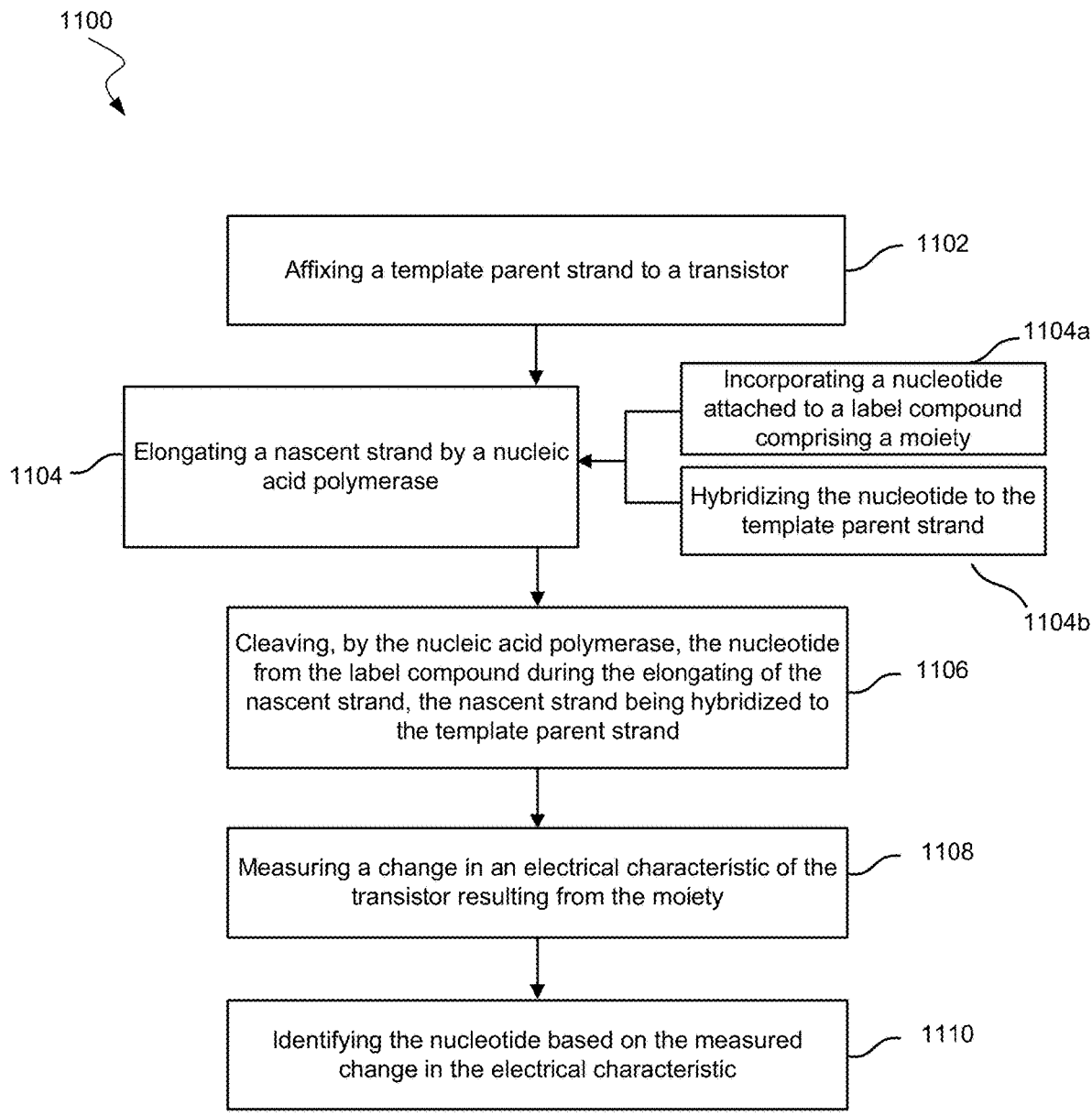
FIG. 11 shows a method of determining a nucleic acid sequence according to embodiments of the present technology.

As shown in FIG. 11, embodiments may include a method 1100 of determining a nucleic acid sequence. Method 1100 may include using system 900.

In block 1102, method 1100 includes affixing a template parent strand to a transistor. In some embodiments, method 1100 may include affixing a plurality of template parent strands to the transistor. Each template parent strand of the plurality of template parent strands may include an identical nucleotide sequence. In some embodiments, the plurality of template parent strands may be affixed to a particle, and then the particle may be affixed to the nanotransistor. The particle may be any particle described herein. In other embodiments, the template parent strands may contact the transistor.

In block 1104, method 1100 may also include elongating a nascent strand by a nucleic acid polymerase. In embodiments with a plurality of template parent strands, methods may include elongating a plurality of nascent strands by a plurality of nucleic acid polymerases.

In block 1104a, method 1100 may include the nucleic acid polymerase incorporating a nucleotide attached to a label compound that includes a moiety. The label compound may be any label compound described herein, and the moiety may be any moiety described herein. Some embodiments may include the plurality of nucleic acid polymerases incorporating a plurality of nucleotides attached to a plurality of label compounds, with each label compound including a moiety. The plurality of nucleotides may be identical nucleotides Each nucleotide of the plurality of nucleotides may be added to each nascent strand of the plurality of nascent strands simultaneously or nearly simultaneously. Nearly simultaneously may mean that each nucleotide may be added to the plurality of nascent strands before a different nucleotide is added to any of the other nascent strands in the plurality of nascent strands.

In block 1104b, method 1100 may include hybridizing the nucleotide to the template parent strand. Block 1104b may be an operation in elongating the nascent strand. In some embodiments, methods may include hybridizing the plurality of nucleotides to the plurality of template parent strands.

In block 1106, the nucleotide is cleaved from the label compound by the nucleic acid polymerase during the elongating of the nascent strand. The nascent strand is hybridized to the template parent strand. In some embodiments, the plurality of nucleotides may be cleaved from the plurality of label compounds by the plurality of nucleic acid polymerases. After cleaving, the moiety or the plurality of moieties may move toward the nanotransistor. For example, as depicted in FIG. 10, moiety 922 and moiety 932 may be in close proximity with nanotransistor 904 at the same time. In some cases, moiety 922 and moiety 932 may contact nanotransistor 904 at the same time. A plurality of label compounds, and therefore a plurality of moieties, near the nanotransistor may increase the probability that the moieties will be in proximity of the nanotransistor. The plurality of label compounds may also increase the effect on the nanotransistor as multiple moieties may combine their field effects on the transistor.

In block 1108, method 1100 may include measuring a change in an electrical characteristic of a nanotransistor resulting from the moiety. Embodiments may also include measuring a change in an electrical characteristic resulting from the plurality of moieties. The electrical characteristic may be any electrical characteristic described herein.

In block 1110, method 1100 may further include identifying the nucleotide based on the measured change in the electrical characteristic. Methods may include identifying the lurality of nucleotides based on the measured change in the electrical characteristic. Identifying the nucleotide or the plurality of nucleotides may include any identification operation described herein.

A plurality of second nucleotides may be incorporated by the plurality of nucleic acid polymerases. Each second nucleotide of the plurality of second nucleotides may be attached to a second label compound that includes a second moiety. The plurality of second label compounds may be cleaved from the second nucleotide by the plurality of nucleic acid polymerases after the second nucleotide is incorporated. The plurality of second moieties may then induce a change in an electrical characteristic of the transistor, which may allow for the second moiety and therefore the second nucleotide to be identified. In this manner, the nucleic acid sequence of the nascent strand may be determined. Accordingly, the nucleic acid sequence of the template parent strand, which is complementary to the nascent strand, may also be determined.

C. Example with Tethered Nucleic Acids

A nucleic acid analysis system, similar to system 900, is used to sequence nucleic acid molecules. The different types of nucleotides are labeled with different moieties. The different moieties, when in proximity of the nanotransistor, show different current signatures. As a result, the nucleotides are identified by the current patterns in the nanotransistor.

IV. Computer System

Figure 12:
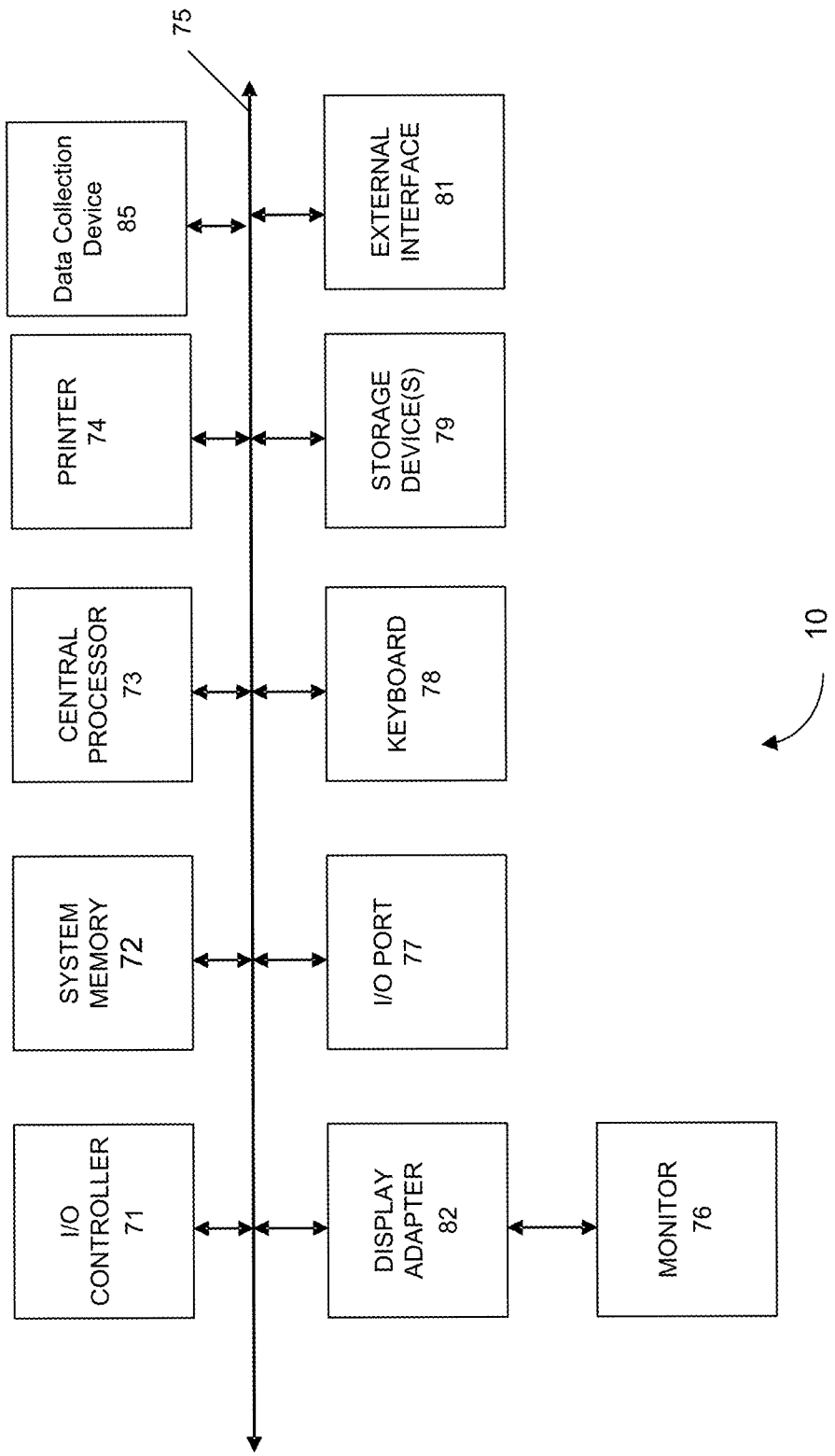
FIG. 12 shows a computer system according to embodiments of the present technology

Any of the computer systems mentioned herein may utilize any suitable number of subsystems. Examples of such subsystems are shown in FIG. 12 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 12 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®, Thunderbolt). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

Figure 13:
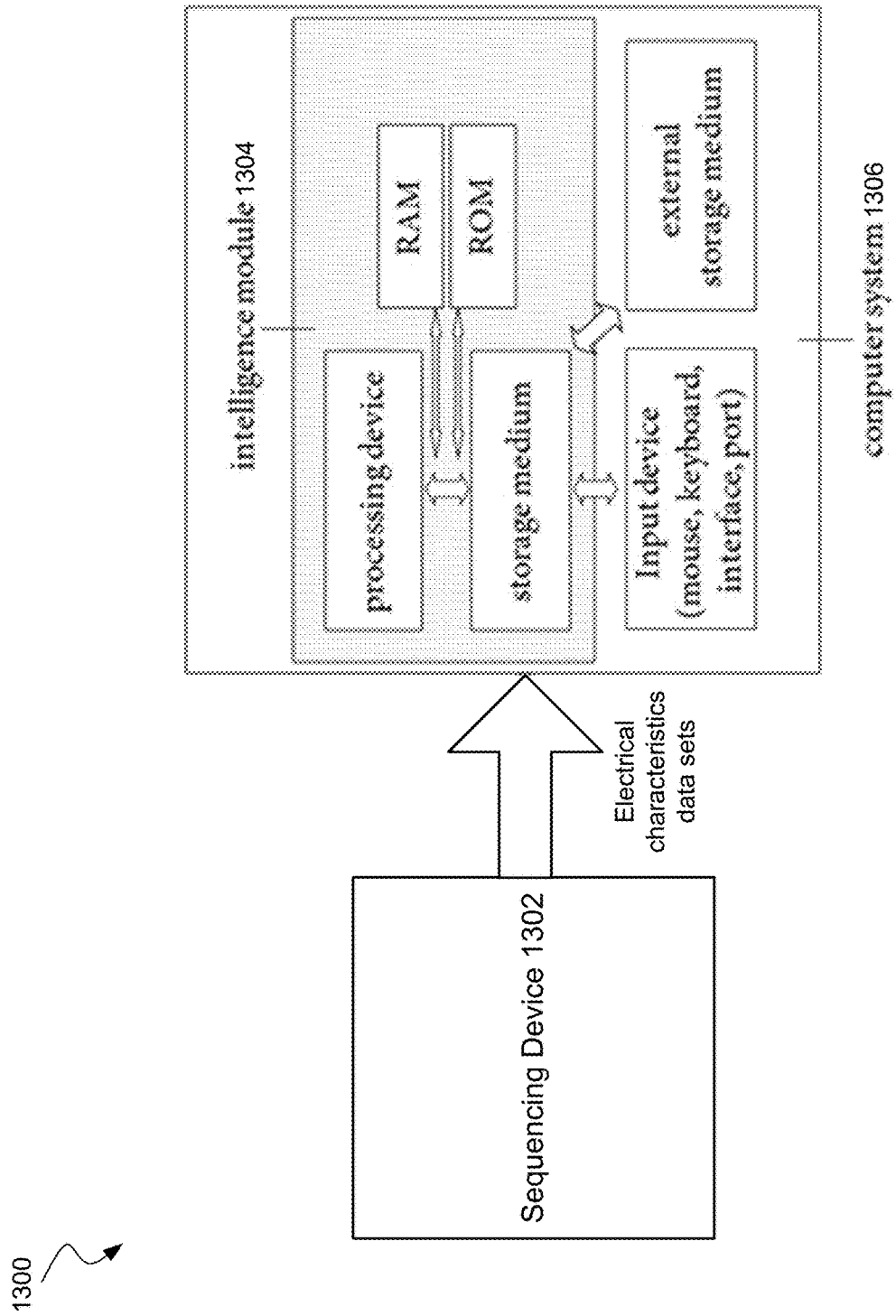
FIG. 13 shows a sequencing system according to embodiments of the present technology.

FIG. 13 shows an exemplary sequencing system. The system depicted in FIG. 13 comprises a sequencing device 1302 and an intelligence module 1304 which is part of the computer system 1306. Sequencing device 1302 may include system 500 or system 900. Computer system 1306 may include parts or all of computer system 10. The data sets (electrical characteristics data sets) are transferred from the sequencing device 1302 to the intelligence module 1304 or vice versa via a network connection or a direct connection. The data sets may for example be processed to identify nucleotides. The identification steps may be implemented by software stored on the hardware of computer system 1306. The data sets may be processed by computer code running on the processor and being stored on the storage device of the intelligence module and after processing transferred back to the storage device of the analysis module, where the modified data may be displayed on a displaying device. In some embodiments, the intelligence module may also be implemented in the sequencing device.

Figure 14:
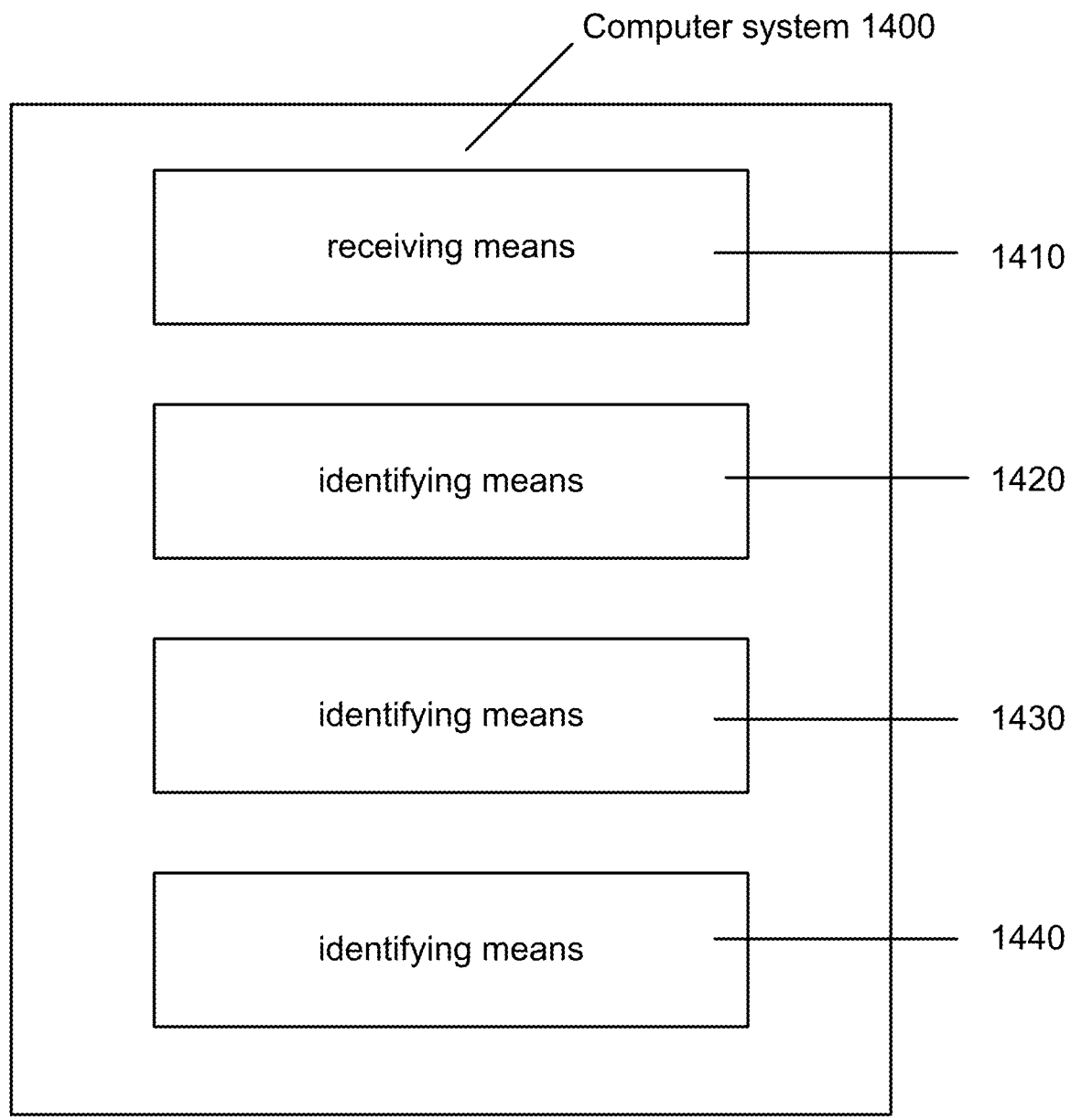
FIG. 14 shows a computer system according to embodiments of the present technology.

FIG. 14 shows that computer system 1400 may comprise receiving means 1410, which may include, for example, receiving electrical characteristic data obtained from a sequencing device. Computer system 1400 may also include identifying means 1420 for identifying a moiety causing a change in the electrical characteristic in the data. Computer system 1400 may also include identifying means 1430 for identifying a nucleotide associated with the moiety. Computer system 1400 may further include identifying means 1440 for identifying a complementary nucleotide of the nucleotide identified with identifying means 1430.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

In the preceding description, for the purposes of explanation, numerous details have been set forth in order to provide an understanding of various embodiments of the present technology. It will be apparent to one skilled in the art, however, that certain embodiments may be practiced without some of these details, or with additional details.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Additionally, details of any specific embodiment may not always be present in variations of that embodiment or may be added to other embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods and reference to "the particle" includes reference to one or more particles and equivalents thereof known to those skilled in the art, and so forth. The invention has now been described in detail for the purposes of clarity and understanding. However, it will be appreciated that certain changes and modifications may be practice within the scope of the appended claims.

All patents, patent applications, publications, and descriptions mentioned herein are incorporated by reference in their entirety for all purposes. None is admitted to be prior art.

What is claimed is:

1. A system for analyzing nucleic acid molecules, the system comprising:
    a transistor comprising a gate electrode in contact with a semiconductor material disposed between a source electrode and a drain electrode;
    a nucleic acid polymerase attached to a tether compound, the nucleic acid polymerase configured to elongate a nascent strand, wherein:
        the tether compound comprises a polymer,
        the polymer is affixed to the transistor,
        the polymer contacts a side of the semiconductor material opposite the gate electrode, and
        the tether compound comprises a nucleic acid strand attached to the polymer, a nucleotide attached to a label compound comprising a moiety;
    a power supply in electrical communication with the transistor; and
    a meter device configured to measure an electrical characteristic of the transistor from the moiety after the nucleic acid polymerase incorporates the nucleotide and after the nucleic acid polymerase cleaves the nucleotide from the label compound.

2. The system of claim 1, wherein:
    the nucleotide is a first nucleotide,
    the moiety is a first moiety, and
    the label compound is a first label compound,
    the system further comprising:
        a second nucleotide attached to a second label compound comprising a second moiety, wherein:
            the second nucleotide is different from the first nucleotide, and
            the second moiety is different from the first moiety.

3. The system of claim 2, wherein:
    the first label compound is one of a plurality of first label compounds, and
    the second label compound is one of a plurality of second label compounds.

4. The system of claim 1, wherein:
    the system comprises a plurality of transistors,
    the power supply is in electrical communication with the plurality of transistors.

5. The system of claim 1, wherein the moiety comprises a metal.

6. A system for analyzing nucleic acid molecules, the system comprising:
    a transistor comprising a gate electrode in contact with a semiconductor material disposed between a source electrode and a drain electrode;
    a template parent strand affixed to a particle, wherein:
        the particle has a diameter or characteristic dimension in a range from 10 nm to 50 nm, and
        the particle contacts a side of the semiconductor material opposite the gate electrode;
    a nucleic acid polymerase configured to elongate a nascent strand hybridized to the template parent strand, wherein the nucleic acid polymerase is not the particle;
    a nucleotide attached to a label compound comprising a moiety;
    a power supply in electrical communication with the transistor; and
    a meter device configured to measure an electrical characteristic of the transistor from the moiety after the nucleic acid polymerase incorporates the nucleotide and after the nucleic acid polymerase cleaves the nucleotide from the label compound.

7. The system of claim 6, further comprising:
    a plurality of template parent strands affixed to the transistor,
    a plurality of nucleic acid polymerases configured to elongate a plurality of nascent strands hybridized to the plurality of template parent strands,
    a plurality of nucleotides attached to a plurality of label compounds, wherein each label compound comprises one moiety of a plurality of moieties.

8. The system of claim 1, wherein:
    the nucleic acid strand is a first nucleic acid strand,
    the label compound comprises a second nucleic acid strand,
    the second nucleic acid strand has a sequence consisting of a first portion of nucleotides and a second portion of nucleotides,
    the first portion of nucleotides is complementary to a first portion of nucleotides of the first nucleic acid strand, and
    the second portion of nucleotides is not complementary to a second portion of nucleotides of the first nucleic acid strand.

9. The system of claim 8, wherein the nucleotide is a first nucleotide,
    the moiety is a first moiety,
    the label compound is a first label compound, and
    the sequence is a first sequence,
    the system further comprising:
        a second nucleotide attached to a second label compound comprising a second moiety, wherein:
            the second nucleotide is different from the first nucleotide,
            the second moiety is the same as the first moiety,
            the second label compound comprises a third nucleic acid strand, the third nucleic acid strand has a second sequence consisting of a first portion of nucleotides and a second portion of nucleotides,
the first portion of nucleotides of the second sequence is complementary to a third portion of nucleotides of the first nucleic acid strand,
the second portion of nucleotides of the second sequence is not complementary to a fourth portion of nucleotides of the first nucleic acid strand, and
the second portion of the second sequence has a different number of nucleotides than the first portion of the first sequence.

10. The system of claim 1, wherein the moiety comprises a halogen or a redox agent.

11. The system of claim 1, wherein the transistor is a semiconducting transition metal dichalcogenide 2D crystal transistor.

12. The system of claim 1, wherein the transistor comprises $MoS_2$, $MoSe_2$, $WS_2$, $WSe_2$, $MoTe_2$, $WTe_2$, $TeS_2$, $SnSe_2$, or $TeSe_2$.

13. The system of claim 1, wherein the transistor is a carbon nanotube transistor.

14. The system of claim 1, wherein the transistor is a graphene transistor.

15. The system of claim 1, wherein the transistor is a silicon nanowire transistor.

16. The system of claim 1, wherein the electrical characteristic is a frequency of current.

17. The system of claim 1, wherein:
the power supply is in electrical communication with the source electrode and the drain electrode, and
the meter device is in electrical communication with the power supply.

* * * * *